United States Patent
Ramu et al.

[11] Patent Number: 5,190,946
[45] Date of Patent: Mar. 2, 1993

[54] METHODS AND COMPOUNDS

[75] Inventors: Avner Ramu, Jerusalem, Israel; Karel Valter, Geneva, Switzerland

[73] Assignee: Hoffmann-La Roche Inc., Nutley, N.J.

[21] Appl. No.: 654,154

[22] Filed: Feb. 12, 1991

[30] Foreign Application Priority Data

Feb. 23, 1990 [GB] United Kingdom ............... 9004099
Feb. 23, 1990 [GB] United Kingdom ............... 9004100
Mar. 30, 1990 [GB] United Kingdom ............... 9007144

[51] Int. Cl.$^5$ .................. A61K 31/495; C07D 295/10
[52] U.S. Cl. ..................... 514/255; 544/396; 544/399; 544/400
[58] Field of Search ............ 544/396, 399, 400; 514/255

[56] References Cited

U.S. PATENT DOCUMENTS

| | | | |
|---|---|---|---|
| 3,378,553 | 3/1968 | Vigelius | 544/399 |
| 4,064,128 | 12/1977 | Milkowski et al. | 544/399 |
| 4,751,298 | 6/1988 | Kleemann et al. | 544/399 |
| 4,880,808 | 11/1989 | Van Daele et al. | 544/399 |
| 5,026,853 | 6/1991 | Van Daele et al. | 544/399 |

FOREIGN PATENT DOCUMENTS 883013 11/1961 United Kingdom .

*Primary Examiner*—Cecilia Tsang
*Attorney, Agent, or Firm*—George M. Gould; George W. Johnston; William Krovatin

[57] ABSTRACT

Compounds of formula $$X-(CHR)_m-N(R^1)-(CH_2)_n-N(R^2)-(CHR^3)_p-Y \qquad I$$

wherein R and $R^3$, which may be the same or different, each is hydrogen, an alkyl group containing 1 to 5 carbon atoms, or an optionally substituted aryl or aralkyl group, substituents being selected from the group consisting of halogen, alkoxy and alkyl groups containing 1 to 5 carbon atoms, said alkyl groups in turn being optionally halo-substituted; $R^1$ and $R^2$, which may be the same or different, each is hydrogen, an alkyl group containing 1 to 5 carbon atoms, or an optionally substituted aryl or aralkyl group, substituents being as indicated above or $R^1$ and $R^2$ taken together are an alkylene group containing 2 or 3 carbon atoms; m and p, which may be the same or different each is a number from 0 to 3; n is the number 2 or 3; and X is a group of the formula $R_x{}^4$—CO—, $R_x{}^4$—COO—, $R_x{}^4$—CONH—, $R_x{}^4$—NHCO—, or $R_x{}^4$—O— and Y is a group of formula $R_y{}^4$—CO—, $R_y{}^4$—COO—, $R_y{}^4$—CONH—, $R_y{}^4$—NHCO—, or $R_y{}^4$—O— which $R_y{}^4$ and $R_x{}^4$, which may be the same of different, each is an optionally substituted aryl, aralkyl or aryloxyalkyl group, substitutents being as indicated above, and the alkyl moiety in the aralkyl and aryloxyalkyl groups containing 1 to 5 carbon atoms and can be optionally substituted by a cyloalkyl group containing 3 to 8 carbon atoms; and physiologically acceptable acid addition salts thereof, have been found to be active in restoring drug-sensitivity to cancer cells that have become multidrug-resistant. They can, therefore, be used as adjuvants in oncology, and they can be administered simultaneously, separately or at intervals in combination with one or more conventional anti-cancer agents for treating malignant tumors and corresponding metastases.

Compounds and salts which have not been previously described in British Patent Specification No. 883013 as well as their preparation and pharmaceutical compositions containing them are also disclosed.

5 Claims, No Drawings

METHODS AND COMPOUNDS

BACKGROUND OF THE INVENTION

In British Patent Specification No. 883013, there are described a number of N,N'-disubstituted piperazines which are stated to have atropinic, anti-histaminic, spasmolytic, anti-emetic and anaesthetic activities.

Surprisingly, it has now been found that a number of diamine derivatives, including those described in British Patent Specification No. 883013, as described in formula I, are active in restoring drug-sensitivity to cancer cells that have become multidrug-resistant. Such compounds, therefore are useful as adjuvants in oncology.

BRIEF SUMMARY OF THE INVENTION

In the broadest aspect of the invention, there is provided the use of a compound of formula I

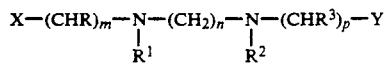

wherein R and $R^3$, which may be the same or different, each is hydrogen, an alkyl group containing 1 to 5 carbon atoms, or an optionally substituted aryl or aralkyl group, substituents being selected from the group consisting of halogen, alkoxy and alkyl groups containing 1 to 5 carbon atoms, said alkyl groups in turn being optionally halo-substituted; $R^1$ and $R^2$, which may be the same or different, each is hydrogen, an alkyl group containing 1 to 5 carbon atoms, or an optionally substituted aryl or aralkyl group, substituents being as indicated above, or $R^1$ and $R^2$ taken together are an alkylene group containing 2 or 3 carbon atoms; m and p, which may be the same or different each is a number from 0 to 3; n is the number 2 or 3; and X is a group of the formula $R_x^4$—CO—, $R_x^4$—COO—, $R_x^4$—CONH—, $R_x^4$—NHCO—, or $R_x^4$—O— and Y is a group of formula $R_y^4$—CO—, $R_y^4$—COO—, $R_y^4$—CONH—, $R_y^4$—NHCO—, or $R_y^4$—O— in which $R_y^4$ and $R_x^4$, which may be the same or different, each is an optionally substituted aryl, aralkyl or aryloxyalkyl group, substituents are as indicated above, and the alkyl moiety in the aralkyl and aryloxyalkyl groups containing 1 to 5 carbon atoms and can be optionally substituted by a cycloalkyl group containing 3 to 8 carbon atoms; or a physiologically acceptable acid addition salt thereof, in the preparation of a medicament for use as an adjuvant in oncology.

DETAILED DESCRIPTION OF THE INVENTION

The invention relates to a method of using the compounds of formula I

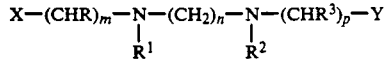

wherein R and $R^3$, which may be the same or different, each is hydrogen, an alkyl group containing 1 to 5 carbon atoms, or an optionally substituted aryl or aralkyl group, substituents being selected from the group consisting of halogen, alkoxy and alkyl groups containing 1 to 5 carbon atoms, said alkyl groups in turn being optionally halo-substituted; $R^1$ and $R^2$, which may be the same or different, each is a hydrogen, an alkyl group containing 1 to 5 carbon atoms, or an optionally substituted aryl or aralkyl group, substituents being as indicated above, or $R^1$ and $R^2$ taken together are an alkylene group containing 2 or 3 carbon atoms; m and p, which may be the same or different each is a number from 0 to 3; n is the number 2 or 3; and X is a group of the formula $R_x^4$—CO—, $R_x^4$—COO—, $R_x^4$—CONH—, $R_x^4$—NHCO—, or $R_x^4$—O— and Y is a group of formula $R_y^4$—CO—, $R_y^4$—COO—, $R_y^4$—CONH—, $R_y^4$—NHCO—, or $R_y^4$—O— in which $R_y^4$ and $R_x^4$, which may be the same or different, each is an optionally substituted aryl, aralkyl or aryloxyalkyl group, substituents are as indicated above, and the alkyl moiety in the aralkyl and aryloxyalkyl groups containing 1 to 5 carbon atoms and can be optionally substituted by a cycloalkyl group containing 3 to 8 carbon atoms; or a physiologically acceptable acid addition salt thereof, as an adjuvant in oncology, that is, as agents for restoring drug-sensitivity to cancer cells that have become multidrug-resistant.

As used herein, alkyl groups containing 1 to 5 carbon atoms include straight and branched chain alkyl groups, for example, methyl, ethyl, propyl and isopropyl groups.

The aryl moiety in the optionally substituted aryl, aralkyl or aryloxyalkyl groups includes, for example, a phenyl or naphthyl group optionally substituted by one or more halogen atoms or $C_{1-3}$ straight or branched chain alkyl or alkoxy groups, such as, 4-methoxyphenyl, 2,6-dimethylphenyl, 3,4,5-trimethoxyphenyl, 3-methoxy-4-n-propoxyphenyl and 4-n-propoxy-1-naphthyl.

The cycloalkyl groups include, for example, cyclopropyl, cyclobutyl, cyclopentyl and cyclohexyl groups.

The term "halogen atom" as used herein includes a fluorine, chlorine, bromine and iodine atom.

The acid addition salts of the compounds of formula I may be those of physiologically acceptable organic or inorganic acids. Preferred acid addition salts are those of hydrochloric acid, though salts of sulfuric, phosphoric, citric, lactic or acetic acid may also be used.

The use of the following compounds is preferred:

Compounds of formula I in which R and $R^3$ each is hydrogen, $R^1$ and $R^2$ each is alkyl, preferably, methyl or ethyl or $R^1$ and $R^2$ taken together are ethylene, and X and Y, which may be the same or different, each is a group of one of the formulas indicated above wherein $R_x^4$ and, respectively, $R_y^4$ is phenyl, phenylalkyl, phenoxyalkyl, diphenylalkyl, phenylcycloalkylalkyl or naphthylalkyl group, the phenyl and naphthyl moieties can be optionally substituted, independently, by 1 to 3 alkoxy and/or alkyl groups and/or halogen atoms, X and/or Y most preferably are 2-phenyl-2-ethylacetoxy, N-2,6-dimethylphenylcarbamoyl, 2-(2-fluorophenyl)-2-ethylacetoxy, 2-(2-methylphenyl)-2-ethylacetoxy, 2-(4-fluorophenyl)-2-ethylacetoxy, 2-(4-chlorophenyl)-2-ethylacetoxy, 2-(2-chlorophenyl)-2-ethylacetoxy, 2-(2-chlorophenyl)-2-ethylacetyl, 2-(3,4-dimethoxyphenyl)-2-ethylacetoxy, 2-phenyl-2-n-propylacetoxy, diphenylacetoxy, 2,2-diphenyl-2-methylacetoxy, 2-(3,4-dimethoxyphenyl)-2-n-propylacetoxy or 2-(3,4-dimethoxyphenyl)-2-n-butylacetoxy and physiologically acceptable acid addition salts thereof.

The use of the following compounds is particularly preferred:

3-[1-(2-phenyl-2-ethylacetoxy)ethyl-4-piperazino]propion-2,6-dimethylanilide;

N,N'-bis[2-[2-(2-fluorophenyl)-2-ethylacetoxy]ethyl]-piperazine;
N,N'-bis[2-[2-(2-methylphenyl)-2-ethylacetoxy]ethyl]-piperazine;
N,N'-bis[2-[2-(4-fluorophenyl)-2-ethylacetoxy]ethyl]-piperazine;
N,N'-bis[2-[2-(4-chlorophenyl)-2-ethylacetoxy]ethyl]-piperazine;
N,N'-bis[2-[2-(2-chlorophenyl)-2-ethylacetoxy]ethyl]-piperazine;
N,N'-bis[2-[2-(3,4-dimethoxyphenyl)-2-ethylacetoxy]ethyl]piperazine;
N,N'-bis[2-(2-n-propyl-2-phenylacetoxy)ethyl]piperazine;
N,N'-bis(2-diphenylacetoxyethyl)piperazine;
N,N'-bis[3-(2-phenyl-2-ethylacetoxy)propyl]piperazine;
N,N'-bis[2-(2-phenyl-2-ethylacetoxy)ethyl]piperazine;
N,N'-bis[2-[2-n-butyl-2-(3,4-dimethoxyphenyl)acetoxy]ethyl]piperazine;
N,N'-bis[2-[2-(3,4-dimethoxyphenyl)-2-propylacetoxy]ethyl]piperazine;
3-[1-(2-diphenylacetoxyethyl)-4-piperazino]propion-2,6-dimethylanilide; and
N,N'-bis[2-(2,2-diphenyl-2-methylacetoxy)ethyl]piperazine; and physiologically acceptable acid addition salts thereof.

The compounds of formula I which are not described in British Patent Specification No. 883013 are those wherein n is other than 2, when $R^1$ and $R^2$ taken together are —(CH$_2$)$_2$—, m and p each is a number from 1 to 3 and R and $R^3$ is a hydrogen or alkyl and the maximum number of carbon atoms contained in each of —(CHR)$_m$— and —(CHR$^3$)$_p$— is 3, and X and Y are a group of the formula

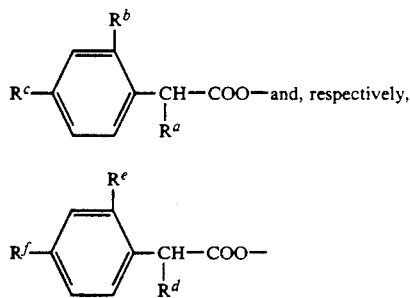

wherein $R^a$ and $R^d$ are hydrogen, alkyl containing from 1 to 5 carbon atoms or aryl or aralkyl and $R^b$, $R^c$, $R^e$ and $R^f$ are hydrogen, halogen or alkoxy containing from 1 to 3 carbon atoms.

The foregoing compounds, which are not described in British Patent Specification No. 883013, also form part of the invention, and they include the following preferred compounds:
3-[1-(2-phenyl-2-ethylacetoxy)ethyl-4-piperazino]propion-2,6-dimethylanilide;
N,N'-bis[2-[2-(2-methylphenyl)-2-ethylacetoxy]ethyl]-piperazine;
N,N'-bis[2-[2-(3,4-dimethoxyphenyl)-2-ethylacetoxy]ethyl]piperazine;
N,N'-bis[2-(2,2-diphenyl-2-methylacetoxy)ethyl]piperazine;
3-[1-(2-diphenylacetoxyethyl)-4-piperazino]propion-2,6-dimethylanilide;
N,N'-bis[2-[2-(3,4-dimethoxyphenyl)-2-propylacetoxy]ethyl]piperazine; and
N,N'-bis[2-[2-n-butyl-2-(3,4-dimethoxyphenyl)acetoxy]ethyl]piperazine;
as well as the following additional representative compounds:
N-[3-(4-n-butoxyphenyl)-3-oxopropyl]-N'-[2-(2-phenyl-2-ethylacetoxy)ethyl]piperazine;
N-[3-(4-methoxyphenoxy)propyl]-N'-[2-(2-phenyl-2-ethylacetoxy)ethyl]piperazine;
N-[2-(2-phenyl-2-ethylacetoxy)ethyl]-N'-(3,4,5-trimethoxybenzoyl)piperazine;
2-[1-(2-phenyl-2-ethylacetoxy)ethyl-4-piperazino]acet-2,6-dimethylanilide;
N,N'-bis[2-(2-phenyl-2-ethylacetoxy)ethyl]-N,N'-dimethylethylenediamine;
N,N'-bis[2-(2-phenyl-2-ethylacetoxy)ethyl]-N,N'-dimethyl-1,3-propylenediamine;
N,N'-bis[2-(2-phenylbutyrylamino)ethyl]piperazine;
N,N'-bis[2-(2-phenyl-2-ethylacetoxy)ethyl]-N,N'-diethylethylenediamine;
N,N'-bis[2-(2-phenyl-2-ethylacetoxy)ethyl]-N,N'-diethyl-1,3-propylenediamine; and
N,N'-bis[2-(2-phenyl-2-ethylacetoxy)ethyl]homopiperazine;
and physiologically acceptable acid addition salts thereof.

In addition to possessing spasmolytic, anticholinergic and local anaesthetic properties, the compounds of formula I are, as mentioned above, active in restoring drug sensitivity to cancer cells that have become multidrug-resistant.

Such cancer cells are characterized by the fact that they are resistant to a large variety of anti-tumour agents and thus become extremely and increasingly difficult to treat. The compounds of formula I, including those described in British Patent Specification No. 883013, and salts thereof lower this resistance and thus greatly increase the effectiveness of drugs conventionally used in chemotherapy. Such properties can be tested according to the method described in Br. J. Cancer 50, 501 (1984) using P388 murine leukemia cells and an adriamycin-resistant subline (P388/ADR).

The Table which follows sets forth for a representative number of compounds of formula I A: the concentration for inhibiting the growth rate of P388 cells by 50% (IC$_{50}$, μM);

B: the IC$_{50}$ for the adriamycin-resistant subline (P388/ADR); and

C: the IC$_{50}$ for P388/ADR cells, measured in the presence of a subtoxic concentration of adriamycin (0.2 μM).

For some of these compounds, the Table also contains toxicity data ("T", LD$_{50}$, mg/kg i.p. after administration of a single dose to mice).

TABLE

| Compound | A | B | C | T |
|---|---|---|---|---|
| 1774 | >60 | >60 | 1.2 | ca. 200 |
| 1775 | 60 | 60 | 1.5 | |
| 1776 | 30 | 30 | 0.8 | 200–400 |
| 1777 | 60 | 60 | 1.2 | |
| 1778 | 30 | 20 | 1.0 | |
| 1779 | 60 | 40 | 1.0 | |
| 1835 | 120 | 120 | 1.2 | ca. 200 |
| 1838 | 20 | 20 | 0.2 | 200–400 |
| 1839 | >60 | >60 | 0.2 | 200–400 |
| 1843 | 7 | 8 | 0.45 | |
| 480 first test | 60 | 60 | 1.2 | 100–200 |
| 480 second test | 20 | 45 | 0.45 | |
| 480 third test | 45 | 60 | 1.0 | |
| 1849 | 12 | 10 | 0.2 | |

TABLE-continued

| Compound | A | B | C | T |
|---|---|---|---|---|
| 1850 | 20 | 20 | 0.2 | |
| 1853 | 60 | 60 | 1.2 | |
| 1854 | 20 | 45 | 0.2 | |

1774 is 3-[1-(2-phenyl-2-ethylacetoxy)ethyl-4-piperazino]propion-2,6-dimethylanilide dihydrochloride;
1775 is N,N'-bis[2-[2-(2-fluorophenyl)-2-ethylacetoxy]ethyl]piperazine dihydrochloride;
1776 is N,N'-bis[2-[2-(2-methylphenyl)-2-ethylacetoxy]ethyl]piperazine dihydrochloride;
1777 is N,N'-bis[2-[2-(4-fluorophenyl)-2-ethylacetoxy]ethyl]piperazine dihydrochloride;
1778 is N,N'-bis[2-[2-(4-chlorophenyl)-2-ethylacetoxy]ethyl]piperazine dihydrochloride;
1779 is N,N'-bis[2-[2-(2-chlorophenyl)-2-ethylacetoxy]ethyl]piperazine dihydrochloride;
1835 is N,N'-bis[2-[2-(3,4-dimethoxyphenyl)-2-ethylacetoxy]ethyl]piperazine dihydrochloride;
1838 is N,N'-bis[2-(2-n-propyl-2-phenylacetoxy)ethyl]piperazine dihydrochloride;
1839 is N,N'-bis(2-diphenylacetoxyethyl)piperazine dihydrochloride;
1843 is N,N'-bis[3-(2-phenyl-2-ethylacetoxy)propyl]piperazine dihydrochloride;
480 is N,N'-bis[2-(2-phenyl-2-ethylacetoxy)ethyl]piperazine dihydrochloride;
1849 is N,N'-bis[2-[2-n-butyl-2-(3,4-dimethoxyphenyl)acetoxy]ethyl]-piperazine dihydrochloride;
1850 is N,N'-bis[2-[2-(3,4-dimethoxyphenyl-2-propylacetoxy]ethyl]-piperazine dihydrochloride;
1853 is 3-[1-(2-diphenylacetoxyethyl)-4-piperazino]propion-2,6-dimethyl-anilide dihydrochloride; and
1854 is N,N'-bis[2-(2,2-diphenyl-2-methylacetoxy)ethyl]piperazine dihydrochloride.

In view of their ability to restore drug sensitivity to cancer cells that have become multidrug-resistant, the compounds of formula I (including those described in British Patent Specification No. 883013) and their physiologically acceptable acid addition salts can be used in the therapy of malignant tumors and corresponding metastases in combination with one or more conventional anti-cancer agents. The compounds of formula I and their physiologically acceptable acid addition salts on the one hand and the conventional anti-cancer agent(s) on the other can be administered simultaneously (in fixed or ad hoc combinations), separately or at intervals.

Conventional anti-cancer agents which can be used in combination with compounds of formula I or their physiologically acceptable acid addition salts include, for example, Vinca alkaloids or epipodophyllotoxins (such as vincristine, vinblastine, vindesine, etoposine, teniposide and the like), antibiotics (such as adriamycin, daunorubicin, bleomycin, mithramicin and the like), interchalators (such as amonafide), antimetabolites (such as fluorouracil), alkylating agents (such as cyclophosphamide, ifosfamide, sulfosfamide, trofosfamide and the like), and the like.

As mentioned above, the compounds of formula I and their physiologically acceptable acid addition salts on the one hand and the conventional anti-cancer agent(s) on the other can be administered simultaneously, separately or at intervals. Preferably, the compounds of formula I and their physiologically acceptable acid addition salts are administered first, conveniently per os, followed by administration of the conventional anti-cancer agent(s), conveniently per os or perenterally. The dose of the conventional anti-cancer agent(s) can be smaller than or similar to that given in conventional therapy. The dose of the compounds of formula I and their physiologically acceptable acid addition salts depends on age, condition and weight of the patient as well as on the route of administration. Normally, appropriate doses of the compounds of formula I and their physiologically acceptable acid addition salts are in the range of from about 1 to about 50 mg/kg body weight for oral administration and in the range of from about 0.1 to about 3 mg/kg body weight for parenteral administration which is conveniently effected by bolus injection or by slow intravenous infusion. However, the aforesaid dosages are only given by way of examples and can be modified by the practitioner, depending on the seriousness of the condition to be treated.

In accordance with the invention, there are also provided compositions containing a compound of formula I or a physiologically acceptable acid addition salt thereof and a conventional anti-cancer agent as a combined preparation for simultaneous, separate or sequential use in the therapy of malignant tumors and corresponding metastases.

In a still further aspect, the invention provides a method of treating malignant tumors and corresponding metastases in mammals which comprises administering to the said subject or host, simultaneously, separately or at intervals, an effective amount of one or more compounds of formula I or physiologically acceptable acid addition salts thereof in combination with one or more conventional anti-cancer agents.

As mentioned earlier, the compounds of formula I which are not described in British Patent Specification No. 833013 also form part of the invention. Such compounds can, in accordance with the present invention, be prepared by (a) reacting a compound of formula

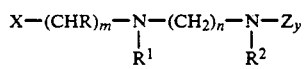

II with a compound of formula

III wherein $R^1$, $R^2$, $R_y^4$, X, R, m and n are as described above and $Z_y$ and $Q_y$ are groups which react together to form a compound of formula I having the desired group —$(CHR^3)_p$—Y; or (b) reacting a compound of formula

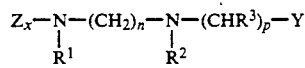

IV with a compound of formula

V wherein $R^1$, $R^2$, Y, n, p and $R_x^4$ are as described above and $Z_x$ and $Q_x$ a group which react together to form a compound of formula I having the desired group X—$(CHR)_m$—; or (c) for the preparation of a compound of formula I in which the groups of formulas X—$(CHR)_m$— and Y—$(CHR^3)_p$— are identical, reacting a compound of formula

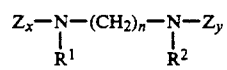

VI wherein $R^1$, $R^2$, $Z_x$, $Z_y$ and n are as described above, $Z_x$ and $Z_y$ are identical, with a compound of formula III (or IV).

For example, if a compound of formula I in which Y is a group of formula $R_y^4$—COO— or $R_y^4$—CONH— is desired, then in the compound of formula II which is used, $Z_y$ may be a group of formula $-(CHR^3)_p-OH$ or $-(CHR^3)_p-NH_2$ and in the compound of formula III which is used, $Q_y$ may be a group of formula $-CO-L$ in which L is a leaving group such as halogen (for example, chlorine) or alkoxy (for example, methoxy or ethoxy).

Similarly, if a compound of formula I in which X is a group of formula $R_x^4-COO-$ or $R_x^4-CONH-$ is desired, then in the compound of formula IV which is used, $Z_x$ may be a group of formula $-(CHR)_m-OH$ or $-(CHR)_m-NH_2$ and in the compound of formula V used, $Q_x$ may be a group as defined above for $Q_y$.

In a process for preparing a compound of formula I;
where, in the starting material of formula III or V which is used, L is halogen, the reaction is conveniently carried out in an anhydrous solvent, such as, chloroform and in the presence of a base, such as, pyridine;
where, in the starting material of formula III or V which is used, L is alkoxy, the reaction is conveniently carried out under conditions conventionally used for a base-catalyzed azeotropic ester exchange, preferably using an organic solvent, for example, dioxane or toluene, and an alkali metal alkoxide, for example, sodium methoxide, as catalyst.

As an alternative example which is to prepare any compound of formula I, in the starting material of formula II which is used, $Z_y$ may be hydrogen atom and in the starting material of formula III which is used, $Q_y$ may be a group of formula:

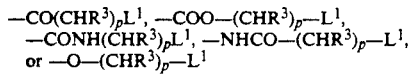

in which $L^1$ is a leaving group, such as, halogen (for example, bromine).

Similarly, to prepare any compound of formula I, in the starting material of formula IV which is used, $Z_x$ may be hydrogen and in the starting material of formula V used which is $Q_x$ may be a group of formula:

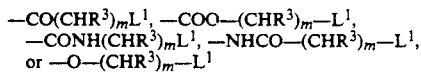

in which $L^1$ is as described above.

In the above processes for the preparation of a compound of formula I, when a starting material of formula III or V is used in which the group $L^1$ is halogen, the reaction is conveniently carried out in an organic amide as solvent, for example, dimethylformamide and in the presence of a base, such as, an alkali metal carbonate or bicarbonate, for example, dry potassium carbonate.

It will be appreciated that it may be possible to prepare a compound of formula I wherein the groups of formula $X-(CHR)_m-$ and $Y-(CHR^3)_p-$ are identical from a starting material of formula VI in a single step. $Z_x$ and $Z_y$ in formula VI are the same and the second reactant is a compound of formula III (or V). This presumes that competing reactions do not cause appreciable problems.

A compound of formula II or IV as described above may readily be prepared by reaction of a compound of formula VI with either a compound $R_x^4-Q_x$ (V) or $R_y^4-Q_y$ (III), wherein the respective end group $Z_y$ or $Z_x$ is as described above, and is optionally protected, the groups $R_x^4$, $R_y^4$, $Q_x$, $Q_y$ are as described above.

It will be apparent that variations and extensions of the methods outlined above are possible, enabling further variations in the substituents to be obtained. It will also be noted that it may be necessary to protect certain sensitive groups during various of the processes, for example, it may be necessary to protect a sensitive $Z_x$ or $Z_y$ group in a compound of formula II or IV, respectively, but such protection and subsequent deprotection is well within the ability of a person skilled in the art.

The compounds of formula I are basic in character and may, if desired, be converted into their acid addition salts. Physiologically acceptable acid addition salts, particularly hydrochlorides, are preferred. These salts may advantageously be prepared by reacting, in approximately stoichiometric proportions, an appropriate inorganic or organic acid with a compound of formula I. The salts may be prepared without intermediate isolation of the corresponding base.

In a another aspect, the invention provides those among the compounds of formula I which are not described in British Patent Specification No. 833013 and physiologically acceptable acid addition salts thereof for use as therapeutically active substances, particularly for use as adjuvants in oncology or as spasmolytics, anticholinergics and local anesthetics; pharmaceutical composition containing these compounds or their salts; and a process for the preparation of such compositions.

The compounds of formula I, including those described in British Patent Specification No. 833013, and physiologically acceptable acid addition salts thereof, can be used as medicaments, for example, in the form of pharmaceutical compositions for enteral or parenteral administration. The compounds of formula I and physiologically acceptable acid addition salts thereof can be administered, for example, perorally, for example, in the form of tablets, coated tablets, dragees, hard and soft gelatin capsules, solutions, emulsions or suspensions; rectally, for example, in the form of suppositories; or parenterally, for example, in the form of injection or infusion solutions, or bolus injections.

The preparation of the pharmaceutical compositions can be effected in a manner which is familiar to a person skilled in the art by bringing the compounds of formula I or physiologically acceptable acid addition salts thereof, optionally in combination with other therapeutically valuable substances (particularly conventional anti-cancer agents), into a galenically administrable form together with suitable, non-toxic, inert, therapeutically compatible solid or liquid carier materials and, if desired, the usual pharmaceutical adjuvants.

As carrier materials, there are suitable not only inorganic carrier materials, but also organic carrier materials. Thus, for tablets, coated tablets, dragees and hard gelatin capsules, there can be used as carrier materials, for example, lactose, maize starch or derivatives thereof, talc, stearic acid or its salts. Suitable carriers for soft gelatin capsules are, for example, vegetable oils, waxes, fats and semi-solid and liquid polyols, depending on the nature of the active substances no carriers are, however, required in the case of soft gelatin capsules. Suitable carrier materials for the preparation of solutions and syrups are, for example, water, polyols, saccharose, invert sugar and glucose. Suitable carrier materials for injection solutions are, for example, water, alcohols, polyols, glycerin and vegetable oils. Suitable carrier materials for suppositories are, for example, natural or hardened oils, waxes, fats and semi-liquid or liquid polyols.

As pharmaceutical adjuvants, there come into consideration the usual preserving agents, solubilizers, stabilizing agents, wetting agents, emulsifying agents, flavor-improving agents such as sweetening agents and flavoring agents, coloring agents, salts for varying the osmotic pressure, buffers, coating agents and antioxidants.

The Examples which follow are intended to illustrate further the invention in more detail, but are not intended to limit its scope in any manner.

EXAMPLE 1

N-[3-(4-n-Butoxyphenyl)-3-oxopropyl]-N'-[2-(2-phenyl-2-ethylacetoxy)ethyl]piperazine dihydrochloride 16.7 g (0.05 mole) of N-3-(4-n-butoxyphenyl)-3-oxopropyl-N'-(2-hydroxyethyl)piperazine (prepared by Mannich reaction from 4-n-butoxyacetophenone and N-(2-hydroxyethyl)piperazine) and 4.75 g (0.06 mole) of pyridine were dissolved in 50 ml of anhydrous chloroform and 10.0 g (0.55 mole) of 2-phenyl-2-ethylacetyl chloride were added dropwise. The mixture was stirred for 1 hour at room temperature, refluxed for 30 minutes and washed with 50 ml of water. The organic phase was separated, dried and evaporated under reduced pressure. The residue was dissolved in a small amount of ethanol and converted into the dihydrochloride by addition of ethanolic HCl. The precipitated title product was recrystallized from ethanol. M.p. 186° C.

EXAMPLE 2

3-[1-(2-Phenyl-2-ethylacetoxy)ethyl-4-piperazino]propion-2,6-dimethylanilide dihydrochloride To a solution of 15.25 g (0.05 mole) of 3-[1-(2-hydroxyethyl)-4-piperazino]propion-2,6-dimethylanilide, prepared from 3-bromopropion-2,6-dimethylanilide and N-(2-hydroxyethyl)piperazine in dimethylformamide in the presence of potassium carbonate, and 4.75 g (0.06 mole) of pyridine in 50 ml of anhydrous chloroform 10.0 g (0.055 mole) of 2-phenyl-2-ethylacetyl chloride were added dropwise. The mixture, treated as indicated in Example 1 yielded the title compound. M.p. 197° C. (ethanol).

EXAMPLE 3

N-[2-(2-Phenyl-2-ethylacetoxy)ethyl]-N'-(3,4,5-trimethoxybenzoyl)piperazine hydrochloride To a solution of 16.2 g (0.05 mole) of N-[2-(2-phenyl-2-ethylacetoxy)ethyl]-N'-(3,4,5-trimethoxybenzoyl)piperazine and 4.75 g (0.06 mole) of pyridine in 50 ml of anhydrous chloroform 10.0 g (0.055 mole) of 2-phenyl-2-ethylacetyl chloride were added dropwise. The reaction mixture, treated as described in Example 1 yield the title product. M.p. 207° C. (ethanol).

EXAMPLE 4

N,N'-Bis[2-[2-(3,4-dimethoxyphenyl)-2-ethyl]acetoxy)ethyl]piperazine dihydrochloride.

To a solution of 11.9 g (0.05 mole) of methyl 2-(3,4-dimethoxyphenyl)-2-ethylacetate and 3.4 g (0.04 mole) of N,N'-bis(2-(hydroxyethyl)piperazine in 100 ml of anhydrous dioxane a solution of 0.1 g of sodium (0.0043 gat) in 1 ml of methanol was added. The residue was dissolved in a small amount of ethanolic HCl and the title product was precipitated with ether. The precipitate was filtered off and recrystallized from ethanol. M.p. 187° C.

EXAMPLE 5

N-[3-(4-Methoxyphenoxy)propyl]-N'-[2-(2-phenyl-2-ethylacetoxy)ethyl]piperazine dihydrochloride.

To a solution of 14.7 g (0.05 mole) of N-(2-hydroxyethyl)-N'-3-(4-methoxyphenoxy)propylpiperazine (prepared from 3-(4-methoxyphenoxy)propylbromide and N-(2-hydroxyethyl)piperazine in dimethylformamide in the presence of potassium carbonate) and 14.25 g (0.075 mole) of methyl 2-phenyl-2-ethylacetate in 100 ml of anhydrous dioxane a solution of 0.1 g of sodium (0.0043 gat) in 1 ml of methanol was added. The solvent was then slowly distilled off over a period of 6 hours. The residue was dissolved in a small amount of ethanolic HCl and the crude title product was precipitated with ether, filtered off and recrystallized from ethanol. M.p. 189° C.

EXAMPLE 6

N,N'-Bis[2-(2-phenyl-2-ethylacetoxy)ethyl]-N,N'-dimethylethylenediamine dihydrochloride To a solution of 4.4 g (0.025 mole) of N,N'-bis(2-hydroxyethyl)-N,N'-dimethylethylenediamine and 14.25 g (0.075 mole) of methyl 2-phenyl-2-ethylacetate in 100 ml of dioxane a solution of 0.1 g (0.0043 gat) of sodium in 1 ml of anhydrous methanol was added. The solvent was then distilled off slowly over a period of 6 hours. The residue treated as indicated in Example 1 yielded the title compound. M.p. 204° C. (ethanol).

EXAMPLE 7

Other compounds which have been prepared by analogous procedures to those described in Examples 1 to 6 include:
a) 2-[1-(2-phenyl-2-ethylacetoxy)ethyl-4-piperazino]acet-2,6-dimethylanilide dihydrochloride, m.p. 244° C. (dec.);
b) N,N'-bis[2-[2-(2-fluorophenyl)-2-ethylacetoxy]ethyl]piperazine dihydrochloride, m.p. 217° C. (dec.);
c) N,N'-bis[2-[2-(2-methylphenyl)-2-ethylacetoxy]ethyl]piperazine dihydrochloride, m.p. 218° C. (dec.);
d) N,N'-bis[2-[2-(4-fluorophenyl)-2-ethylacetoxy]ethyl]piperazine dihydrochloride, m.p. 214° C. (dec.);
e) N,N'-bis[2-[2-(4-chlorophenyl)-2-ethylacetoxy]ethyl]piperazine dihydrochloride, m.p. 212° C. (dec.);
f) N,N'-bis[2-[2-(2-chlorophenyl)-2-ethylacetoxy]ethyl]piperazine dihydrochloride, m.p. 205° C. (dec.);
g) N-2-[2-(2-chlorophenyl)-2-ethylacetoxy]ethyl-N'-2-(2-chlorophenyl)-2-ethylacetylpiperazine hydrochloride, m.p. 169° C. (dec.);
h) N,N'-bis[2-(2-phenyl-2-ethylacetoxy)ethyl]-N,N'-dimethyl-1,3-propylenediamine dichlorhydride, m.p. 182° C. (ethanol);
i) N,N'-bis[2-(2-phenylbutyrylamino)ethyl]piperazine dichlorhydride, m.p. 227° C. (dec.) (ethanol); base m.p. 149° C. (ethyl acetate);
j) N,N'-bis[3-(2-phenyl-2-ethylacetoxy)propyl]piperazine dichlorhydride, m.p. 228° C. (dec.) (ethanol);
k) N,N'-bis[3-(2-phenylbutyrylamino)propyl]piperazine, m.p. 144° C.(ethyl acetate), dichlorhydride, m.p. 210° C. (dec.) (ethanol);
l) N,N'-bis[2-(2-phenyl-2-ethylacetoxy)ethyl]-N,N'-diethylethylenediamine dichlorhydride, m.p. 132° C. (ethanol), dihydrogenoxalate, m.p. 106° C. (ethanol);
m) N,N'-bis[2-(2-phenyl-2-ethylacetoxy)ethyl]-N,N'-diethyl-1,3-propylenediamine dihydrogenoxalate, m.p. 112° C. (ethanol);

n) N,N'-bis[2-(2-phenoxybutyryloxy)ethyl]piperazine dichlorhydride, m.p. 180° C. (dec.) (ethanol);

o) N,N'-bis[2-(2-phenyl-2-ethylacetoxy)ethyl]homopiperazine dihydrogenmaleinate, m.p. 107°-108° C. (ethanol);

p) 3-[1-(2-diphenylacetoxyethyl)-4-piperazino]propion-2,6-dimethylanilide dihydrochloride, m.p. 191.5° C. (isopropanol);

q) N,N'-bis[2-(2,2-diphenyl-2-methylacetoxy)ethyl]piperazine dihydrochloride, m.p. 300° C. (dec);

r) N,N'-bis[2-[2-n-butyl-2-(3,4-dimethoxyphenyl)acetoxy]ethyl]piperazine dihydrochloride, m.p. 158° C. (isopropanol); and s) N,N'-bis[2-[2-(3,4-dimethoxyphenyl)-2-propylacetoxy]ethyl]piperazine dihydrochloride, m.p. 185° C. (isopropanol).

EXAMPLE 8

Still other compounds which may be prepared by procedures analogous to those described in Examples 1 to 6 include:

N-[2-[bis(3-methoxy-4-n-propoxyphenyl)acetamino]ethyl]-N'-(3,4,5-trimethoxybenzyl)piperazine dihydrochloride;

N,N'-bis[2-[bis(3-methoxy-4-n-propoxyphenyl)acetylamino]ethyl]piperazine dihydrochloride;

N,N'-bis[5,5-bis(3-methoxy-4-n-propoxyphenyl)-4-oxapentyl]piperazine dihydrochloride;

N,N'-bis[5-cyclohexyl-4-oxo-5-(3,4,5-trimethoxyphenyl)pentyl]piperazine dihydrochloride;

N-[3-[bis(3-methoxy-4-n-propoxyphenyl)acetylamino]propyl]-N'-[2-(3,4,5-trimethoxyphenylcarbamoyloxy)ethyl]piperazine dihydrochloride; and N-[2-[2-(4-(n-propoxy-1-naphthyl)-2-propylacetylamino)ethyl]-N'-[2-[bis(4-ethoxyphenyl)acetylamino]ethyl]piperazine dihydrochloride.

EXAMPLE 9

Pharmaceutical formulations of the following composition and containing as the active substance 3-[1-(2-phenyl-2-ethylacetoxy)ethyl-4-piperazino]propion-2,6-dimethylanilide dihydrochloride;

N,N'-bis[2-[2-(3,4-dimethoxyphenyl)-2-ethylacetoxy]ethyl]piperazine dihydrochloride;

N,N'-bis[2-[2-(3,4-dimethoxyphenyl)-2-propylacetoxy]ethyl]piperazine dihydrochloride;

3-[1-(2-diphenylacetoxyethyl)-4-piperazino]propion-2,6-dimethylanilide dihydrochloride; or N,N'-bis[2-(2-phenyl-2-ethylacetoxy)ethyl]piperazine dihydrochloride can be prepared in a manner which is familiar to any person skilled in the art.

| a) Tablets | per tablet |
|---|---|
| Active substance | 275 mg |
| Lactose | 135 mg |
| Maize starch | 70 mg |
| Polyvinylpyrrolidone | 15 mg |
| Talc | 3 mg |
| Magnesium stearate | 2 mg |
| Tablet weight | 500 mg |

| b) Capsules | per capsule |
|---|---|
| Active substance | 370 mg |
| Lactose | 100 mg |
| Maize starch | 20 mg |
| Talc | 9 mg |
| Magnesium stearate | 1 mg |
| Capsule fill | 500 mg |

| c) Injection solution | per 5 ml of solution |
|---|---|
| Active substance | 40 mg |
| Sodium chloride | 42,5 mg |
| Water for injection q.s. ad | 5 ml |

| d) Infusion solution* | per 250 ml of solution |
|---|---|
| Active substance | 300 mg |
| Vincristine sulfate | 3 mg |
| Physiological sodium chloride solution q.s. ad | 250 ml |

*containing, in addition to the active substance, that is, a physiologically acceptable acid addition salt of a compound of formula I, a conventional anti-cancer agent

We claim:

1. A method of restoring drug-sensitivity to cancer cells that have become multi drug-resistant in a host requiring such treatment which comprises administering to the host an effective amount of a compound of formula I

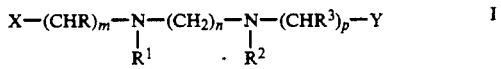

wherein R and $R^3$, which may be the same or different, each is hydrogen, an alkyl group containing 1 to 5 carbon atoms, or unsubstituted or substituted aryl or aralkyl, wherein the substituents are selected from the group consisting of halogen, alkoxy and alkyl in turn being unsubstituted or halo-substituted; $R^1$ and $R^2$ taken together are alkylene containing 2 carbon atoms; m and p, which may be the same or different, each is a number from 0 to 3; n is the number 2; and X is a group of the formula $R_x^4$ —CO—, $R_x^4$—COO—, $R_x^4$ —CONH—, $R_x^4$ —NHCO—, or $R_x^4$ —O— and Y is a group of formula $R_y^4$—CO—, $R_y^4$—COO—, $R_y^4$—CONH—, $R_y^4$ —NHCO—, or $R_y^4$ —O— in which $R_x^4$ and $R_y^4$, which may be same or different, each is unsubstituted or substituted aryl, aralkyl, diarylalkyl or aryloxyalkyl, wherein the substituents are as indicated above, and the alkyl moiety in the aralkyl, diarylalkyl and aryloxyalkyl groups contains 1 to 5 carbon atoms and can be unsubstituted or substituted by a cycloalkyl group containing 3 to 8 carbon atoms; or a physiologically acceptable acid addition salt thereof.

2. A method according to claim 1, wherein in formula I R and $R^3$ each is hydrogen; and $R_x^4$ and, respectively, $R_y^4$, which may be same or different, are phenyl, phenylalkyl, phenoxyalkyl, diphenylalkyl, phenylcycloalkylalkyl or naphthylalkyl wherein the phenyl or naphthyl moiety is unsubstituted or is bearing up to 3 substituents selected from the group consisting of alkoxy, alkyl and halogen.

3. A method according to claim 2, wherein X and/or Y each is 2-phenyl-2-ethylacetoxy, N-2,6-dimethylphenylcarbamoyl, 2-(2-fluorophenyl)-2-ethylacetoxy, 2-(2-methylphenyl)-2-ethylacetoxy, 2-(4-fluorophenyl)-2-ethylacetoxy, 2-(4-chlorophenyl)-2-ethylacetoxy, 2-(2-chlorophenyl)-2-ethylacetoxy, 2-(2-chlorophenyl)-2-ethylacetyl, 2-(3,4-dimethoxyphenyl)-2-ethylacetoxy, 2-phenyl-2-n-propylacetoxy, diphenylacetoxy, 2,2-diphenyl-2-methylacetoxy, 2-(3,4-dimethoxyphenyl)-2-n-propylacetoxy, or 2-(3,4-dimethoxyphenyl)-2-n-butylacetoxy.

4. A method according to claim 1, wherein the compound of formula I is selected from the group consisting of:

3-[1-(2-phenyl-2-ethylacetoxy)ethyl-4-piperazino]-propion-2,6-dimethylanilide;

N,N'-bis[2-[2-(2-fluorophenyl)-2-ethylacetoxy]ethyl]piperazine;

N,N'-bis[2-[2-(2-methylphenyl)-2-ethylacetoxy]ethyl]piperazine;

N,N'-bis[2-[2-(4-fluorophenyl)-2-ethylacetoxy]ethyl]piperazine;

N,N'-bis[2-[2-(4-chlorophenyl)-2-ethylacetoxy]ethyl]piperazine;

N,N'-bis[2-[2-(2-chlorophenyl)-2-ethylacetoxy]ethyl]piperazine;

N,N'-bis[2-[2-(3,4-dimethoxyphenyl)-2-ethylacetoxy]ethyl]piperazine;

N,N'-bis[2-(2-n-propyl-2-phenylacetoxy)ethyl]piperazine;

N,N'-bis(2-diphenylacetoxyethyl)piperazine;

N,N'-bis[3-(2-phenyl-2-ethylacetoxy)propyl]piperazine;

N,N'-bis[2-(2-phenyl-2-ethylacetoxy)ethyl]piperazine;

N,N'-bis[2-[2-n-butyl-2-(3,4-dimethoxyphenyl)acetoxy]ethyl]piperazine;

N,N'-bis[2-[2-(3,4-dimethoxyphenyl)-2-propylacetoxy]ethyl]piperazine;

3-[1-(2-diphenylacetoxyethyl)-4-piperazino]propion-2,6-dimethylanilide; or

N,N'-bis[2-(2,2-diphenyl-2-methylacetoxy)ethyl]piperazine;

or a physiologically acceptable acid addition salt thereof.

5. A method according to claim 4, wherein the compound of formula I is N,N'-bis(2-diphenylacetoxyethyl)piperazine.

* * * * *

UNITED STATES PATENT AND TRADEMARK OFFICE
CERTIFICATE OF CORRECTION

PATENT NO. : 5,190,946
DATED : March 2, 1993
INVENTOR(S) : Avner Ramu and Karel Valter It is certified that error appears in the above-identified patent and that said Letters Patent is hereby corrected as shown below:

In claim 2, column 12, line 48, "A method according to claim 1, wherein in formula 1 R and $R^3$ each is hydrogen; and $R_x^4$ and, respectively, $R_y^4$, which may be same or different, are phenyl, phenylalkyl, phenoxyalkyl, diphenylalkyl, phenylcycloalkylalkyl or naphthylalkyl wherein the phenyl or naphthyl moiety is unsubstituted or is bearing up to 3 substituents selected from the group consisting of alkoxy, alkyl and halogen."

should read

-- A method according to claim 1, wherein in formula 1 R and $R^3$ each is hydrogen; $R^1$ and $R^2$ each is alkyl or $R^1$ and $R^2$ taken together are ethylene; and $R_x^4$ and, respectively, $R_y^4$, which may be same or different, are phenyl, phenylalkyl, phenoxyalkyl, diphenylalkyl, phenylcycloalkylalkyl or naphthylalkyl wherein the phenyl or naphthyl moiety is unsubstituted or is bearing up to 3 substituents selected from the group consisting of alkoxy, alkyl and halogen --

Signed and Sealed this

Nineteenth Day of April, 1994

Attest:

BRUCE LEHMAN

Attesting Officer  Commissioner of Patents and Trademarks